United States Patent [19]

Colvin et al.

[11] Patent Number: 5,010,892
[45] Date of Patent: Apr. 30, 1991

[54] BODY LUMEN MEASURING INSTRUMENT

[75] Inventors: David P. Colvin, Apex; Raymond A. Whitney, Raleigh, both of N.C.; Bernard R. Marsh, Upperco, Md.; William M. Kline, Gloversville, N.Y.; Ronald R. Rizzo, Gloversville, N.Y.; Mark E. Orlosky, Gloversville, N.Y.

[73] Assignees: Triangle Research and Development Corp., Research Triangle Park, N.C.; Johns Hopkins University, Baltimore, Md.; Medical Evaluation Devices & Instruments Corp., Gloversville, N.Y.

[21] Appl. No.: 189,998

[22] Filed: May 4, 1988

[51] Int. Cl.$^5$ .............................................. A61B 5/103
[52] U.S. Cl. ...................................... 128/774; 128/780
[58] Field of Search .................. 128/772, 774–781, 128/207.15, 341, 345; 604/100, 104–107, 163, 164, 170, 171, 280

[56] References Cited

U.S. PATENT DOCUMENTS

| | | | |
|---|---|---|---|
| 2,269,963 | 1/1942 | Wappler | 128/217 |
| 3,674,006 | 7/1972 | Holmer | 128/1.2 |
| 3,738,388 | 6/1973 | Salvatore | 128/774 |
| 4,016,867 | 4/1977 | King et al. | 128/778 |
| 4,121,572 | 10/1978 | Kvceminski | 128/778 |
| 4,204,548 | 5/1980 | Kurz | 128/778 |
| 4,224,951 | 9/1980 | Hasson | 128/778 |
| 4,294,264 | 10/1981 | Fischell et al. | 128/778 |
| 4,328,811 | 5/1982 | Fogarty | 128/774 |
| 4,449,522 | 5/1984 | Baum | 128/207.15 |
| 4,489,732 | 12/1984 | Hasson | 128/778 |
| 4,500,313 | 2/1985 | Young | 128/774 |
| 4,563,176 | 1/1986 | Gustavsson et al. | 104/171 |
| 4,566,465 | 1/1986 | Arnan et al. | 128/774 |
| 4,572,162 | 2/1986 | Livesay et al. | 128/1 R |
| 4,643,194 | 2/1987 | Fogarty | 128/668 |

FOREIGN PATENT DOCUMENTS

| | | | |
|---|---|---|---|
| 2840633 | 3/1980 | Fed. Rep. of Germany | 128/778 |
| 3231863 | 3/1984 | Fed. Rep. of Germany | 128/778 |
| 0733650 | 5/1980 | U.S.S.R. | 128/774 |
| 0736949 | 5/1980 | U.S.S.R. | 128/780 |

Primary Examiner—David J. Isabella
Assistant Examiner—K. M. Reichle
Attorney, Agent, or Firm—Richard E. Jenkins

[57] ABSTRACT

A body lumen measuring instrument for insertion into a body passageway such as a bronchial tube or the like in order to determine the interior lumen diameter and/or axial length of the passageway at a predetermined location. This instrument can also be used to aid selection of a radioisotope capsule of proper size to be properly positioned at a specific location for tumor treatment. The measuring instrument includes a flexible sleeve having a handle secured to one end. A cable is slidably positioned within the sleeve and secured at one end to a slide actuator within the handle and at the other end terminates in a probe adapted for determining body passageway size under endoscopic observation. A measurement scale is associated with an indicator on the slide actuator in order to display the passageway size.

2 Claims, 1 Drawing Sheet

BODY LUMEN MEASURING INSTRUMENT

DESCRIPTION

1. Technical Field

The present invention relates to an instrument for measuring certain size characteristics of body lumens and, more particularly, to an instrument usable to determine passageway dimensions, obstacle and malignant lesion sizes as well as to select the correct size of implantable radioisotope capsule and to facilitate accurate positioning thereof in the bronchus

2. Background Art

There are presently over 100,000 deaths per year in the United States from bronchial carcinoma. Conventional treatments for bronchial carcinoma or lung cancer include surgery, radiation therapy and chemotherapy. Interstitial irradiation has been shown to be promising for the local treatment of certain tumors assuming that the dose rate of radiation delivered from a stereotaxically implanted source is sufficiently high that tumor cells receive a critical threshold dose during a complete cell cycle. This requirement can be met by using high-activity radioisotopes which can be removed from the site after the dose is delivered thereto. It is known to utilize radioactive sources encased within catheters which may be removed after the desired dose is delivered by a catheter which is made to precisely hold the radioactive source at the tumor target site. It is also known to utilize a capsule such as that disclosed in U.S. Pat. No. 4,584,991 to Tokita, et al. for positioning a radioactive source adjacent a tumor in a body cavity.

In view of the advantages of using an implanted radioactive source containing capsule in order to treat tumors in body lumens or cavities, the need has developed for an instrument which is capable of accurate transbronchoscopic measurement of lesion size and lumen diameter in order to permit better assessment of tumor growth and regression as well as the selection of the proper size of radioisotope capsule for insertion into the bronchus or other body passageway. Proper size selection assures that the radioisotope capsule can be placed into and removed from a body lumen as necessary with minimized difficulties.

The body lumen measuring instrument of the present invention particularly lends itself for use in facilitating localized, endobronchial radiotherapy treatment for a bronchial malignancy with radioisotope capsules. Applicant believes that his inventive instrument can be used to measure a variety of body lumens as well as both site and obstacle sizes, and that it is superior to any known device to serve this much needed purpose. Usage is applicable to any endoscope as well as a fiberoptic bronchoscope.

DISCLOSURE OF THE INVENTION

In accordance with the present invention, applicant provides a body lumen measuring instrument adapted to be utilized in ascertaining size characteristics of body passageways, most particularly the bronchus, as well as malignant lesions therein in order to facilitate placement of a radioisotope capsule in the passageway to irradiate the malignant tumor therein. More specifically, in order to assure the proper positioning and security of a selected radioisotope capsule in the bronchus in order to address a malignant tumor, it has been found necessary that an accurate measurement be made of the bronchial diameter as well as the bronchial axial length where the radioisotope capsule will be positioned. Although this can be attempted with endoscopic assessment, the enhanced depth of field of an endoscope's optics makes this dimensional determination very difficult. Therefore, applicant has developed an instrument which is particularly adapted to accurately measure lumen diameter at a given position as well as the axial length available for insertion of a radioisotope capsule.

The measuring instrument of the invention comprises an elongated flexible sleeve adapted to be inserted into a body passageway and a handle secured to the proximal end of the sleeve. A cable is slidably positioned within the sleeve and includes probe means at the distal end remote from the handle for determining passageway or lumen size characteristics. Means are provided on the handle for selectively extending the cable so as to extend and withdraw the probe means, and an associated measurement scale is provided adjacent thereto which provides passageway size measurements corresponding to movement by the probe means when the probe means contacts the lumen wall as observed through to endoscope.

Accordingly, it is an object of the body lumen measuring instrument of the invention to provide for a measuring instrument which is capable of measuring both passageway diameter and axially extending space to aid in the insertion of a proper size radioisotope capsule in order to treat a malignant tumor.

BRIEF DESCRIPTION OF THE DRAWINGS

Some of the objects of the invention having been stated, other objects will become evident as the description proceeds, when taken in connection with the accompanying drawings, in which.

BEST MODE FOR CARRYING OUT THE INVENTION

Figure 1:
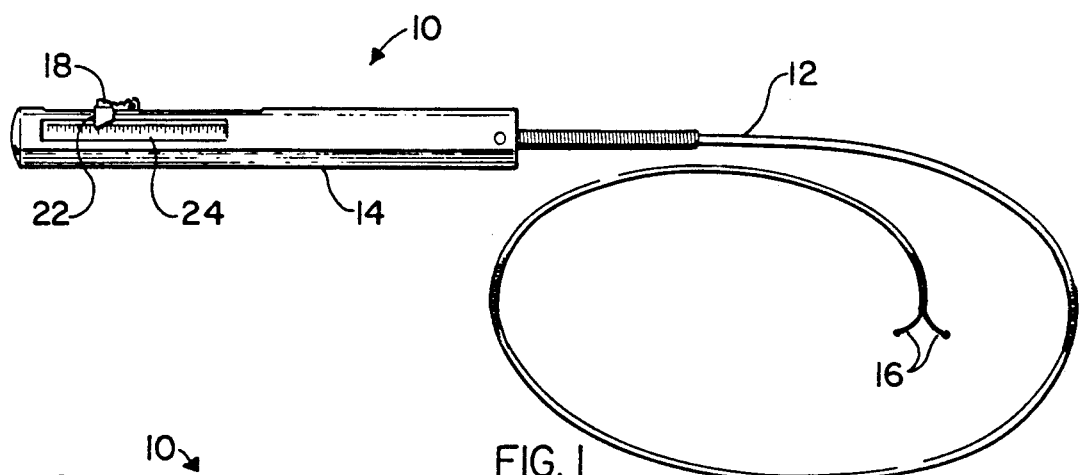
FIG. 1 is a side elevation view of a preferred embodiment of the instrument of the present invention.
Figure 2:
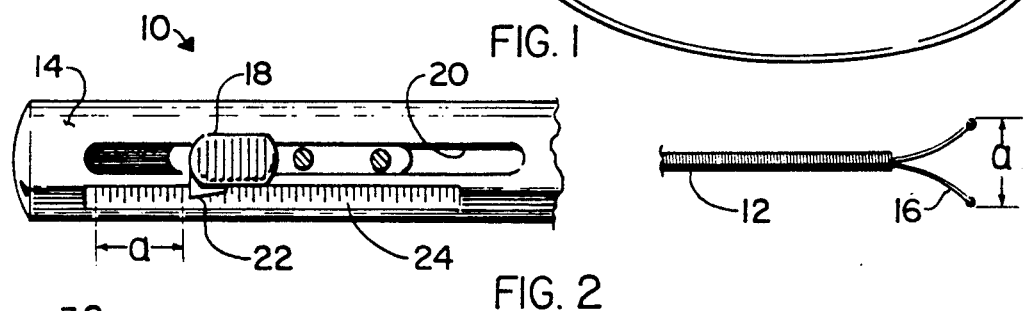
FIG. 2 is an enlarged top plan view, with parts broken away, of the measuring instrument shown in FIG. 1.

Referring now to the drawings, FIG. 1 and FIG. 2 illustrate a preferred embodiment of the body lumen measuring instrument, generally designated 10, made according to the invention. Measuring instrument 10 consists of sleeve 12 to which handle 14 is attached. Sleeve 12 is flexible and most suitably comprises a metal sheathed catheter. A flexible cable 16 is slidably positioned within sleeve 12 and comprises a bifurcated probe at the distal end remote from the handle and at the other proximal end extends into handle 14. The bifurcated probe, best shown in FIG. 2, consists of a flexible, resilient wire of high yield strength having a memory for an outwardly curved shape when slidably extended from sleeve 12. This resilient wire can be designed to have maximum stored spring energy per unit length in order to minimize the required length for a given lateral spread. When withdrawn into sleeve 12, the bifurcated probe wires are straightened so as to extend substantially along the longitudinal axis of the sleeve. Although not shown in the drawings, it is contemplated that cable 16 may be a single wire terminating in the bifurcated probe as best seen in FIG. 2, although the cable could also consist of two resilient wires each terminating in a respective one of the two probe elements of the bifurcated probe.

Cable 16 is connected at the proximal end remote from the bifurcated probe and within handle 14 to slide 18 which can be slidably moved within slot 20 along the longitudinal axis of handle 14. It is understood that slide 18 is conventional in design and may be accomplished in any suitable manner which provides for selective extension and withdrawal of the bifurcated probe end of cable 16 within sleeve 12. As also shown in FIGS. 1 and 2, slide 18 includes a pointer 22 which traverses measurement scale 24 affixed to handle 14. By observing the movement of pointer 22 along measurement scale 24 as cable 16 and the associated bifurcated probe are extended from sleeve 12 into contact with a body passageway, the diameter of the body passageway (dimension a in FIG. 2) can be determined since the scale is carefully calibrated so that movement of the bifurcated probe of cable 16 into contact position with a body passageway as observed through the endoscope, will provide a related reading on measurement scale 24 of the diameter of the passageway. Readout could also be accomplished with a digital display.

Figure 3:
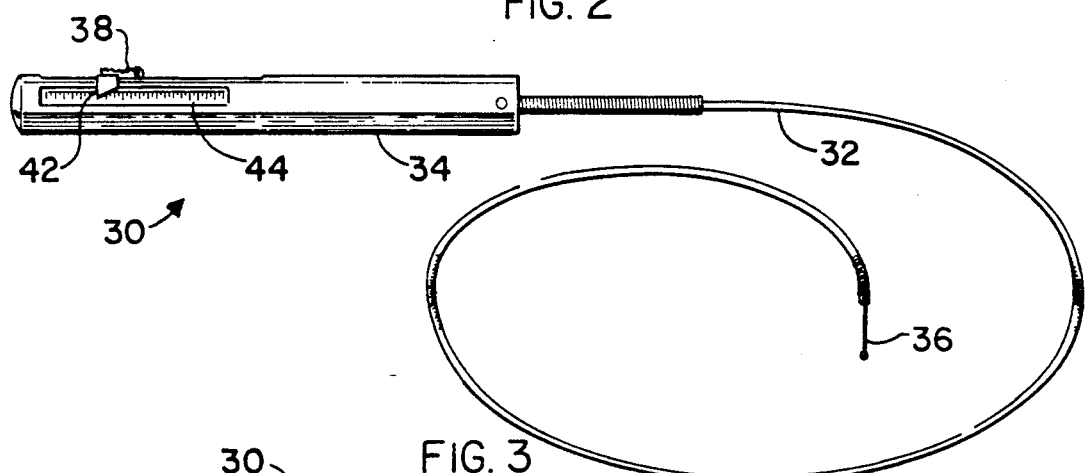
FIG. 3 is a side elevation view of a second embodiment of the present invention.
Figure 4:
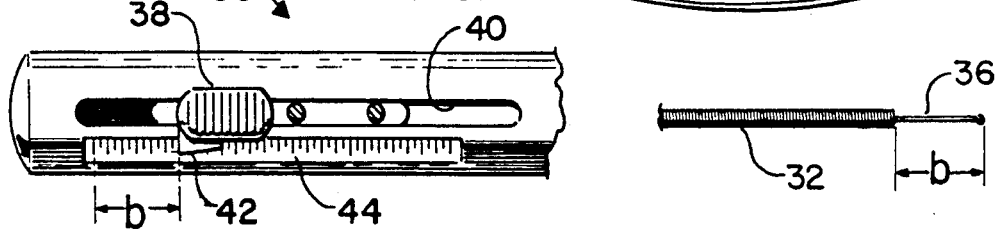
FIG. 4 is an enlarged top plan view, with parts broken away, of the instrument shown in FIG. 3.

A second embodiment of the body passageway measuring instrument is shown in FIGS. 3 and 4 and is generally designated 30. Measuring instrument 30 consists of flexible sleeve 32 connected at its proximal end to handle 34. A resilient cable 36 is slidably positioned within flexible sleeve 32 and has a probe at the distal end extending generally coaxially outwardly from sleeve 32. Cable 36 is connected at the proximal end to slide 38 which is adapted to be moved within longitudinally extending slot 40 within handle 34. A pointer 42 and corresponding measurement scale 44 are also provided and function in the same fashion as those provided in the measuring instrument shown in FIGS. 1 and 2.

Measuring instrument 30 is substantially identical to measuring instrument 10 in all respects other than the probe at the remote or distal end of resilient cable 36. Whereas measuring instrument 10 utilizes a bifurcated probe in order to determine passageway inner diameter a or other lateral dimensions, measuring instrument 30 consists of a probe which extends coaxially outwardly from sleeve 32 so as to facilitate linear measurements between the end of sleeve 32 and the end of cable 36 (dimension b) such as for lesion length and the axial length available within a bronchial tube within which to position a radioisotope capsule. In other words, measuring instrument 10 is adapted to determine bronchial diameter or lateral measurements and measuring instrument 30 is adapted to measure bronchial axial length at a location where it is desired to place a radioisotope capsule in order to treat a malignant tumor or the like in the lung. Of course, although the instruments have been described in terms of bronchial measurements, it is clearly contemplated that the inventive apparatus can be used to make measurements in other body passageways and for purposes other than placement of a radioisotope capsule in the body passageway (including obstacle size determinations).

Figure 5:
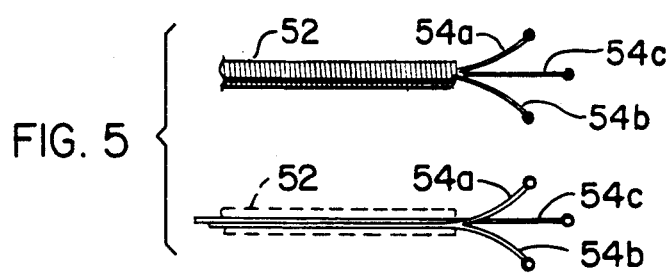
FIG. 5 is an enlarged view of the probe end of a third embodiment of the measuring instrument of the present invention.

Still another embodiment of the present invention can be appreciated with reference now to FIG. 5 illustrating the end of flexible sleeve 52 remote from a handle similar to those illustrated in previous drawings and wherein the cable terminates in a probe consisting of two probes 54A, 54B having a memory for a radially outwardly extending shape and a third probe 54C extending generally coaxially outwardly from flexible sleeve 52. This dual purpose measuring instrument would serve to measure both lumen diameter and axial length with a single instrument. Spherical tips are provided at the end of each probe, and were also provided on the probes of instruments 10 and 30, in order to facilitate visual confirmation of probe contact with the inner bronchus walls. Although not illustrated in the drawings and being a matter of design choice, it is contemplated that probes 54A, 54B will merge into a single cable connected to a slide having a corresponding measurement scale and probe 54C will be the terminal extension of a second cable connected to a separate slide with a corresponding measurement scale. Most suitably the instrument will be capable of measuring bronchial diameter and axial length up to 25 millimeters with an accuracy of plus or minus 1 millimeter.

It will be understood that various details of the invention may be changed without departing from the scope of the invention. Furthermore, the foregoing description is for the purpose of illustration only, and not for the purpose of limitation—the invention being defined by the claims.

What is claimed is:

1. An instrument for determining size characteristics of body lumens or passageways or the like and comprising:
    an elongated flexible sleeve adapted to be inserted into a body lumen or passageway or the like;
    a handle secured to one end of said flexible sleeve;
    an elongated cable slidably received within said sleeve and including probe means for determining body lumen or passageway or the like size characteristics at one end thereof; means cooperatively associated with said handle for sliding said cable within said sleeve so as to selectively extend and withdraw said probe means from the other end of the sleeve, wherein said elongated cable comprises a first cable, wherein said probe means comprises at least one resilient wire connected at one end thereof to said cable and having a normally curved shape so that said at least one wire extends generally radially outwardly from the other end of said flexible sleeve remote from said handle when extended by said sliding means, wherein said elongated cable further comprises a second cable and wherein said probe means also comprises at least one resilient wire connected at one end thereof to said second cable and extending generally coaxially outwardly from the end of said flexible sleeve when extended by said sliding means; and
    measurement means mounted on said handle and cooperatively associated with said cable sliding means for measuring movement by said probe means.

2. An instrument according to claim 1 wherein each of said resilient wires includes an enlarged spherically-shaped element at its free end.

* * * * *